United States Patent
Gaillard et al.

(10) Patent No.: US 12,128,127 B2
(45) Date of Patent: Oct. 29, 2024

(54) EXTRACTS OF PLANTS CONTAINING POLYGODIAL, COMPOSITIONS COMPRISING SUCH EXTRACTS AND COSMETIC AND/OR DERMATOLOGICAL USES THEREOF

(71) Applicant: ROBERTET SA, Grasse (FR)

(72) Inventors: Emmanuelle Gaillard, Landevant (FR); Christine Perichet, Grasse (FR); Marina Humbert, Grasse (FR); Sophie Lavoine, Mouans-Sartoux (FR); Irène Lamour, Vannes (FR)

(73) Assignee: ROBERTET SA, Grasse (FR)

( * ) Notice: Subject to any disclaimer, the term of this patent is extended or adjusted under 35 U.S.C. 154(b) by 1052 days.

(21) Appl. No.: 17/046,823

(22) PCT Filed: Mar. 29, 2019

(86) PCT No.: PCT/EP2019/057971
§ 371 (c)(1),
(2) Date: Oct. 12, 2020

(87) PCT Pub. No.: WO2019/197173
PCT Pub. Date: Oct. 17, 2019

(65) Prior Publication Data
US 2021/0177727 A1    Jun. 17, 2021

(30) Foreign Application Priority Data
Apr. 13, 2018  (FR) .................................. 1870450

(51) Int. Cl.
*A61K 8/97* (2017.01)
*A61K 9/00* (2006.01)
*A61K 31/11* (2006.01)
*A61K 36/28* (2006.01)
*A61K 36/704* (2006.01)
*B01D 11/02* (2006.01)

(52) U.S. Cl.
CPC .............. *A61K 8/97* (2013.01); *A61K 9/0014* (2013.01); *A61K 31/11* (2013.01); *A61K 36/28* (2013.01); *A61K 36/704* (2013.01); *B01D 11/0203* (2013.01); *B01D 11/0284* (2013.01); *B01D 11/0292* (2013.01)

(58) Field of Classification Search
None
See application file for complete search history.

(56) References Cited

U.S. PATENT DOCUMENTS

| 5,523,105 A | 6/1996 | Ishikawa et al. |
| 2014/0248379 A1* | 9/2014 | Mueller ............... A61K 36/185 424/725 |
| 2019/0060785 A1* | 2/2019 | Durward ............ B01D 11/0203 |

FOREIGN PATENT DOCUMENTS

| JP | 2003073264 A | 3/2003 |
| JP | 2004083488 A | 3/2004 |
| KR | 20120031625 A | 4/2012 |

OTHER PUBLICATIONS

Garland S, Journal of Essential Oil Research, 28(1), 55-63, Sub-critical carbon dioxide extraction of the hexane extract of the leaves Tasmannia Lanceolata (Year: 2015).*
Garland et al (Journal of Essential Oil Research, 2016, 28(1), 55-63) (Year: 2016).*
Canna-pet® (https://canna-pet.com/articles/what-is-co2-extraction) (Year: 2015).*
Sandra M. Garland et al., "Sub-critical carbon dioxide extraction of the hexane extract of the leaves of Tasmannia Lanceolata", The Journal of Essential Oil Research: JEOR, UK., Jan. 2, 2016, pp. 55-63, vol. 28 No. 1 (Abstract Only).
"Pore Delete Instant Surface Perfector", www.gupd.com, Mar. 13, 2017.
PCT, International Search Report and Written Opinion; International Application No. PCT/EP2019/057971, Jul. 18, 2019, 12 Pages.
PCT, English Translation of International Search Report; International Application No. PCT/EP2019/057971, Jul. 18, 2019, 3 Pages.

* cited by examiner

*Primary Examiner* — Celeste A Roney
(74) *Attorney, Agent, or Firm* — FisherBroyles, LLP; Susan M. Oiler (57) ABSTRACT

An extract of a plant chosen from *Tasmannia lanceolata, Drimys winteri, Spilanthes acmella* and *Polygonum hydropiper* is obtained from ground and dried leaves of said plant by supercritical $CO_2$ extraction at a pressure of between 120 and 350 bar and at a temperature from 35 to 60° C. and contains polygodial. A process for obtaining such an extract is disclosed along with compositions comprising, in a physiologically acceptable medium, an effective amount of the extract to promotes wound healing and decrease inflammation in skin disorders.

4 Claims, 5 Drawing Sheets

EXTRACTS OF PLANTS CONTAINING POLYGODIAL, COMPOSITIONS COMPRISING SUCH EXTRACTS AND COSMETIC AND/OR DERMATOLOGICAL USES THEREOF

CROSS-REFERENCE TO RELATED APPLICATIONS

The present invention is filed under 35 U.S.C. § 371 as the U.S. national phase of International Patent Application No. PCT/EP2019/057971, filed Mar. 29, 2019, which designated the United States and which claims the benefit of French Patent Application No. 1870450 filed Apr. 13, 2018, which is hereby incorporated in its entirety including all tables, figures, and claims.

This invention relates to the area of cosmetic and/or dermatological active ingredients. More particularly, it relates to an extract obtained from a plant chosen from *Tasmannia lanceolata, Drimys winteri, Spilanthes acmella* and *Polygonum hydropiper*, as well as the process of obtaining it, the compositions comprising extracts from such plants and their cosmetic and/or dermatological uses.

*Tasmannia lanceolata* (also known by the name of *Drimys aromatica* or *Drimys lanceolata*, and commonly known as Tasmanian pepper, mountain pepper or Cornish pepper leaf) is a wild plant of the Winteraceae family, native to northern Tasmania.

It is an evergreen shrub. The leaves are lanceolate, usually 4 to 8 cm long and 1 to 2 cm wide, dark green, very shiny, with a matte, light-coloured underside. The young stems are red in colour. Usually in June, the small cream-coloured flowers, with 5 narrow, waxy petals, appear grouped together at the end of the branches. The species is dioecious, each shrub is male or female. The female flowers are easily recognised by their ovary, a small green ball in the centre of the flower. When this flower is fertilised, the fruit is rounded into two lobes and reddens. It turns black when ripe. Both sexes are needed for fructification and *Tasmannia lanceolata* is adorned with beautiful, fleshy, very decorative bunches which are red to black in colour.

*Tasmannia lanceolata* is mainly used in the food industry as a condiment as a substitute for pepper, for example for its ground and dried leaves and its berries.

*Tasmannia lanceolata*, in particular its roots, is also used in traditional Chinese medicine and is used in complex formulations of compositions with many other plant extracts.

As an example, we can cite the document CN107582791 which discloses a composition comprising in particular *Tasmannia lanceolata* roots for the treatment of amenorrhoea.

We can also cite the document CN107412567 which describes the use of *Tasmannia lanceolata*, the ripe fruit in particular, in a composition for the treatment of itchy skin.

In addition, Garland et al. document ("Sub-critical carbon dioxide extraction of the hexane extract of the leaves of *Tasmannia lanceolata*", The Journal of Essential Oil Research, Vol. 28 No. 1, 2 Jan. 2016) describes the subcritical $CO_2$ extraction of a hexane extract from the leaves of *Tasmannia lanceolata*, the extract containing polygodial.

Document JP2004083488 describes an extract of *Polygonum hydropiper* Linne obtained by extraction in a solvent at 80° C. for 3 hours under stirring, and concentrated under reduced pressure at 40° C. after filtration and then finally dried (example 1).

Document JP2003073264 describes an extract of *Tasmannia lanceolata* obtained by extracting dried leaves in 10 volumes of methanol heated under reflux for 3 hours, filtering and evaporating under reduced pressure and then adding distilled water and ethyl acetate to obtain the extract after separation.

Document KR20120031625 describes the plant *Persicaria hydropiper* L. Spach, the fruit of which is known to treat abdominal pain, oedema and wounds. The fruit appears to contain 0.13% essential oil, the main ingredients of which are tadeonone (polygodial), isotadeonal, confertifoline and polygonone.

Document U.S. Pat. No. 5,523,105 describes a plant extract containing polygodial by extraction of a dry powder of, for example, *Polygonum hydropiper, Drimys lanceolata* or *Warburgia stublmannii*, successively with petroleum ether and methanol, the extract obtained being further purified by liquid chromatography. This document also describes a plant extract containing a polygodial obtained from a dry plant by the same process using other organic solvents, such as hexane, ethyl ether, acetone, ethanol and methanol, and concentrated under reduced pressure.

Therefore, such documents do not disclose a plant extract containing polygodial to treat skin disorders such as scars and/or stretch marks.

Otherwise, to treat skin disorders such as scars and/or stretch marks, there are many topical treatments based for example on silicone, corticosteroids such as cortisone, retinoids such as tretinoin or hyaluronic acid.

However, occlusive treatment with a silicone dressing requires several months of use with a minimum of 12 hours of occlusion per day. The main side effects found were irritation, pruritus and skin maceration.

The main short-term side effects of corticosteroids are increased appetite, weight gain, water retention, a tendency to aggressiveness with insomnia and nervousness, aggravation of depression, and frequently a temporary imbalance of diabetes or hypertension.

Regarding retinoids, they are known to be photosensitive, especially isotretinoin. They are also potentially irritant substances, especially tretinoin.

In contrast to other substances, hyaluronic acid presents almost no risk of side effects. Nevertheless, allergenic risks may arise. Also, hyaluronic acid is often administered by injection.

Other active ingredients known to have an effect on skin healing include allantoin, zinc oxide, D-panthenol, aloe vera and hydrocotyl.

There are also other techniques that are relatively expensive and require specialist intervention, including peels, micro-dermabrasion, micro-puncture, and fractional ablative or non-ablative laser treatment.

Considering the above, a problem to be solved by the invention proposes is to develop a plant extract, that is non-phototoxic and non-irritating to the skin, which has a wound healing and anti-inflammatory activity aimed at reducing, partially or totally, the irregularities on the skin surface without presenting the side effects of known treatments.

The invention therefore has as first object an extract of a plant chosen from *Tasmannia lanceolata, Drimys winteri, Spilanthes acmella* and *Polygonum hydropiper*, characterised in that it is able to be obtained from the ground and dried leaves of said plant by extraction with supercritical $CO_2$ at a pressure of between 120 and 350 bar and at a temperature of between 35 and 60° C. and in that it contains polygodial.

However, although extracts in accordance with the known prior art may contain polygodial, due to the specific properties of supercritical $CO_2$, the extract obtained according to the invention has a different composition from those obtained by subcritical $CO_2$ extraction of a hexane extract or by the so-called classical processes (solvent, liquid or hydrodistillation extraction), with an increased quality.

In addition, the invention has as second object a composition comprising, in a physiologically acceptable medium, an effective amount of an extract obtained according to the invention, for use in promoting wound healing and decreasing inflammation in skin disorders.

The last object of the invention is a process for obtaining an extract of a plant chosen from *Tasmannia lanceolata, Drimys winteri, Spilanthes acmella* and *Polygonum hydropiper*, characterised in that it comprises the following steps:
- extracting leaves or berries, preferably leaves, from said plant with supercritical $CO_2$ at a pressure of between 120 and 350 bar, preferably between 150 and 285 bar, and at a temperature of between 35 and 60° C., preferably between 40 and 50° C.; and
- recovering said extract containing polygodial.

In this description, unless otherwise specified, it is understood that, when an interval is given, it includes the upper and lower limits of that interval.

The invention and the advantages deriving therefrom will be better understood by reading the following description and the non-limiting methods of implementation that follow, written in relation to the appended figures in which.

The invention relates to an extract of a plant chosen from *Tasmannia lanceolata, Drimys winteri, Spilanthes acmella* and *Polygonum hydropiper*.

The preferred extracted plant is *Tasmannia lanceolata*.

The extract according to the invention is obtained from a solid material, more particularly from ground and dried leaves of said plant by extraction with supercritical carbon dioxide (SC $CO_2$) at a pressure of between 120 and 350 bar and at a temperature of between 35 and 60° C.

Such an extract according to the invention contains polygodial.

Supercritical fluid extraction, and more particularly supercritical $CO_2$, is advantageously used as an alternative to solvent extraction or subcritical $CO_2$ extraction processes.

$CO_2$ as a supercritical fluid has significant advantages: it is neutral, non-toxic, non-polluting and non-flammable, making it a so-called "green" solvent. It is also widely available at very high levels of purity and at a moderate cost, it is easy to remove and thus leaves no residue in the extract. In addition, its critical parameters are low (Tc=31° C., Pc=73.8 bar).

The principle of plant extraction using SC $CO_2$ is based on the strong variation in the solvent power of $CO_2$ according to the operating conditions (temperature and pressure), which allows the molecules to be extracted selectively according to their chemical nature. As it is very weakly polar, $CO_2$ proves to be an excellent solvent for apolar or low-polar molecules under supercritical conditions. Based on this principle, once the desired compound has been dissolved in the SC $CO_2$ medium, it is easy to obtain the pure extract by simple depressurisation which then leads to the separation of the $CO_2$, which has become gaseous again, and the extract, which is recovered in liquid or solid form.

This process makes it possible to avoid solvent residue removal operations (extraction, impregnation, formulation), which are essential when the solvent is an organic compound. In addition, the low temperatures used, below 60° C., make it possible to preserve the chemical integrity of the treated heat-sensitive molecules and to minimise operating costs. These properties make supercritical $CO_2$ extraction an environmentally and economically viable alternative to distillation processes.

The extract according to the invention is preferably obtained by supercritical $CO_2$ extraction at a pressure of between 150 and 285 bar, for example 150, 170, 200, 230, 250 or 285 bar, and at a temperature of between 40 and 50° C., for example 40, 45 or 50° C.

Extraction is advantageously carried out at a $CO_2$ per load rate at a ratio of 10 to 40 kg/kg.

The extract according to the invention is preferably obtained from leaves or berries of plants chosen from *Tasmannia lanceolata, Drimys winteri, Spilanthes acmella* and *Polygonum hydropiper*.

The extract according to the invention is more preferably obtained from leaves, advantageously ground, even more advantageously finely ground.

The leaves are used fresh, semi-dry (wilted) or dried, preferably dried under standard conditions known to the skilled person.

An alcoholic co-solvent, for example ethanol with a content of between 0 and 10%, may be advantageously used to obtain the extract according to the invention.

Advantageously, a decolouring stage for the extract according to the invention thus obtained by supercritical $CO_2$ extraction can also be further carried out.

As non-restrictive illustrative examples, decolouring can be carried out with vegetable black, by molecular distillation, or by vacuum fractionation.

The extract obtained according to the invention can be advantageously formulated in a suitable carrier, for example a lipophilic carrier, such as miglyol, triethylcitrate, glycerin, triacetin, monopropylene glycol or vegetable oils. For example, the extract according to the invention is formulated in 95% lipophilic carrier.

The extract according to the invention, obtained by extraction with supercritical $CO_2$, thus contains an unsaturated sesquiterpene dialdehyde of particular interest called polygodial (CAS 6754-20-7) with the formula:

The harmlessness of such an extract according to the invention, for example an extract advantageously of ground and dried leaves of *Tasmannia lanceolata,* has been demonstrated through various toxicological tests.

The extract according to the invention is non-phototoxic, non-irritating to the skin and moderately irritating to the eyes (HET-CAM test).

In addition, the Ames test, a biological test for determining the mutagenic potential of such an extract according to the invention also classified the extract as non-mutagenic.

This invention also relates to the cosmetic and/or dermatological fields, in particular that of wound healing and/or anti-inflammatory products.

For this purpose, another object of the invention relates to a composition, for example a cosmetic and/or dermatological composition, comprising, in a physiologically acceptable medium, an effective amount of an extract obtained according to the invention, for use in promoting wound healing and decreasing the inflammation in skin disorders.

The extract used in the composition according to the invention, obtained from such plants, contains polygodial.

Surprisingly, the extract obtained from such plants chosen from *Tasmannia lanceolata, Drimys winteri, Spilanthes acmella* and *Polygonum hydropiper,* preferably from *Tasmannia lanceolata* and more preferably from the leaves, advantageously ground and dried, of *Tasmannia lanceolata,* showed novel wound healing and anti-inflammatory activities.

A physiologically acceptable medium means a medium suitable for use in contact with human and animal cells, in particular epidermal cells, free from toxicity, irritation, undue allergic response and similar, and is proportionate to a reasonable benefit/risk ratio.

Such a physiologically acceptable medium may comprise excipients known and used in cosmetic and dermatological fields. The skilled person shall take care to choose the physiologically acceptable medium so that it does not interfere with the interesting properties of the extract and the compositions according to the invention.

The extract used in the composition according to the invention may be obtained by any type of extraction.

Non-restrictive examples of extraction include techniques known to the skilled person in the field such as hydrodistillation, dry steam training, extraction by volatile solvent(s) such as hexane, methanol, ethanol taken alone or in mixture with water, maceration, infusion, decoction, percolation, extraction with supercritical $CO_2$.

The extract used in the composition according to the invention is preferably obtained by a process comprising the following steps:

supercritical $CO_2$ extraction at a pressure of between 120 and 350 bar, preferably between 150 and 285 bar, and at a temperature of between 35 and 60° C., preferably between 40 and 50° C.; and recovering said extract containing polygodial.

The extract preferably used in the composition according to the invention comprises a polygodial concentration of between 0.1% and 10%, preferably between 0.2% and 5%, more preferably between 0.5% and 3% by weight of the total weight of the extract, for example 0.5%, 1%, 1.5%, 2%, 2.5% or 3%.

The extract used in the composition according to the invention is preferably obtained from leaves or berries of such plants chosen from *Tasmannia lanceolata, Drimys winteri, Spilanthes acmella* and *Polygonum hydropiper,* more preferably leaves, advantageously ground, even more advantageously finely ground.

The extract used in the composition according to the invention may be obtained from fresh, semi-dry (wilted) or dried leaves, preferably from leaves dried under standard conditions known to the skilled person.

The composition used according to the invention comprises such an extract of a plant chosen from *Tasmannia lanceolata, Drimys winteri, Spilanthes acmella* and *Polygonum hydropiper* at a concentration of between 0.01 and 20% by weight of the total weight of the composition, preferably between 0.1% and 10%, for example 1%, 2%, 5% and 10%.

The composition used according to the invention is formulated to be administered orally or to be applied topically to the skin.

The skin is an organ composed of several layers of tissue, which, among other things, acts as the body's protective covering. It provides a physical barrier that protects the underlying tissues and organs from external physical, chemical and biological attack. Anatomically speaking, the skin has two main parts. The thin superficial layer, the epidermis, attached to a thicker internal layer: the dermis. A third, deeper layer constitutes the hypodermis but is not traditionally regarded a layer of the skin. The whole skin and the appendages (i.e. nails, hair) make up the integument.

The skin can also refer to the scalp.

Skin does not therefore refer to the underlying tissues in continuity with the skin such as mucous membranes.

The composition used according to the invention is therefore not intended to be applied to mucous membranes.

The composition used according to the invention may be formulated in a form suitable for oral administration, for example as a food supplement.

The oral dosage forms used may be solid or liquid. Solid oral forms are usually tablets, hard pills (capsules), soft capsules, sachets containing powder or granules. Oral liquid forms are usually oral solutions, syrups, elixirs, oral emulsions, oral suspensions or oral drops.

Preferably, the oral composition used according to the invention is in the form of a soft capsule.

The composition used according to the invention may be in various forms acceptable for topical application, in particular in solid or liquid form, depending on the physiologically acceptable medium used.

The topical composition may be in the form of a water-in-oil (W/O) or oil-in-water (O/W) type emulsion, suspension, oil, gel, paste, cream, lotion, solution, serum, for example an aqueous, alcoholic, aqueous-alcoholic or fatty solution, powder.

Preferably, the topical composition according to the invention is in the form of an oil, cream, gel or serum.

The composition according to the invention comprising an effective amount of an extract of a plant chosen from *Tasmannia lanceolata, Drimys winteri, Spilanthes acmella* and *Polygonum hydropiper* is used to promote wound healing and decrease inflammation in skin disorders.

Skin disorders are defined as alterations or irregularities in the surface of the skin, which may result from physiological problems, resolved or unresolved, or caused by physical or chemical treatments.

Alterations or disorders of the skin surface, including skin irregularities, are for example selected from those associated with acneic skin, signs of skin ageing, weight gain, weight loss, or pregnancy. They may also be caused by physical or chemical treatments, whether cosmetic or pharmaceutical, or caused by skin disorders, where alterations or irregularities of the skin remain after said disorders have been physiologically resolved.

The skin wound healing process contains several distinct phases.

The initial phase is accompanied by a strong vascular response of vasoconstriction followed by an increase in capillary permeability and vasodilation. Thrombin and extravascular collagen contribute to the aggregation and activation of platelets in the clot. Many proteins are brought by the influx of blood to the site of injury, allowing the fibrin clot to form. The fibrin-fibronectin network provides a reservoir for the many growth factors released in the wound (PDGF, bFGF, TGFa,β) that are responsible for the activation of neutrophils and macrophages. These cells will then fight the infection, clean the wound and participate in local renutrition.

Then, the inflammatory phase is accompanied by vasodilation leading to redness and sensations of heat and pain. Neutrophils and monocytes are attracted to the wound not only by platelet-released factors, but also by bacterial peptides, complement factors and fibrin degradation products. Neutrophils are the first leukocytes present in the wound; they release proteolytic enzymes such as elastase and collagenases and have a local anti-infectious function. Monocytes bind to endothelial cells and migrate into the wound. Once in the tissue medium, they differentiate into macrophages and adhere to proteins in the extracellular matrix; but above all, like platelets, they are a source of cytokines such as IGF, TGF, TNF or PDGF. These substances amplify the inflammatory response and stimulate the proliferation of fibroblasts, the production of collagen and, more broadly, the proliferation of granulation tissue.

This phase corresponds to the transition from inflammation to wound healing by secreting growth factors that stimulate cell proliferation and matrix tissue formation.

The tissue repair phase then takes place with the formation of granulation tissue. This phase lasts 10 to 15 days and corresponds to the proliferation of fibroblasts, angiogenesis and synthesis of the extracellular matrix. This phase is largely dependent on cytokines (IGF1, EGF, TNFa, TGFβ, PDGF-BB) which promote fibroblast migration and proliferation. Fibroblasts synthesise a new extra-cellular matrix initially composed mainly of type III collagen, fibronectin, proteoglycans (hyaluronic acid, chondroitin sulphate . . . ). They also participate in matrix remodelling by producing proteolytic enzymes including metalloproteinases. The matrix also serves as a reservoir of growth factors.

This is followed by re-epithelialisation which takes place in several phases: migration of epithelial cells from the banks or annex, their multiplication and differentiation of the reformed epidermis.

The keratinocytes migrate onto the matrix components and allow the re-epithelialisation of the wound. Once the wound is closed by a monolayer of keratinocytes, the keratinocytes stop their migration, multiply and differentiate.

The final phase of skin wound healing corresponds to the maturation of the scar with the tissues being remodelled due to the reorganisation of the neosynthesised collagen fibres which will eventually re-form a healthy tissue. The remodelling of the extracellular matrix goes through an inflammatory and proliferative phase for up to two months after the wound closes. Little by little the granulation tissue becomes scarce in fibroblasts, a denser collagenous structure appears, while the vascular network is organised. Matrix remodelling will increase the resistance of the scar considerably, up to 80-90% of its initial strength by the sixth week. Fibronectin and hyaluronic acid are gradually replaced by collagens, elastic fibres and glycosaminoglycans (GAGs).

Age, tension forces and pressure influence the synthesis and organisation of collagen molecules. The scars are nevertheless, in all cases, less resistant and less elastic than normal skin, partly due to a certain lack of elastin.

The composition of the extracellular matrix plays an important role in the migration of inflammatory cells, in the differentiation of connective cells and epithelial cells. The healing process is characterised by significant changes in the extracellular matrix.

During wound healing, the extracellular matrix contains GAGs, fibronectin and type III collagen.

The end of the wound healing process is characterised by:
a gradual decrease in fibronectin concentration;
a modification of the GAG composition of the extracellular matrix;
a degradation of type III collagen, replaced by type I collagen.

Fibronectin stimulates the migration of endothelial cells and fibroblasts into the inflammatory site.

The composition according to the invention is preferably used to prevent and/or promote scar reduction.

The composition according to the invention is also preferably used to prevent and/or promote the reduction of stretch marks.

Stretch marks appear as parallel linear or spindle-shaped striae 1 or more cm long by 1 mm to 1 cm wide. They are depressed and covered with a wrinkled epidermis of a pearly white colour (in the case of old stretch marks) or of a pink or purple colour (in the case of recent stretch marks). They are almost always multiple and symmetrical, and their direction is generally radiated on the breasts, vertical and oblique on the flanks, transverse on the lumbo-sacral region.

The mechanism of stretch mark formation was initially perceived as solely the result of elastic tissue rupture after significant mechanical tension. In fact, stretch marks seem to result first and foremost from fibroblast damage. In stretch marks, over-expression of interferon gamma at the expense of TGF-β has been shown to prevent correct fibroblast function and good quality wound healing. The consequences consist of a degeneration of collagen (stretched and atrophic collagen bundles) and elastic fibres (thick and winding at the periphery of stretch marks and reduction of the superficial network) responsible for a decrease in the thickness of the dermis.

The composition according to the invention is more preferably used to reduce the depth and colouring of stretch marks as well as to increase the density and thickness of the dermis of stretch marks.

The invention is illustrated hereafter, without any restriction, with an example of embodiment, examples of formulations of a composition containing an extract of *Tasmannia lanceolata* obtained according to the invention and results of biological activities.

Example 1

Process for Obtaining an Extract of *Tasmannia lanceolata* by Supercritical $CO_2$ Extraction According to an example of the preferred embodiment of the invention, the extract is obtained from leaves of *Tasmannia lanceolata*. 250 kg of dried and crushed leaves are extracted with supercritical $CO_2$ at a pressure of 290 bar and a temperature of 45° C. with an ethanol co-solvent ratio of 4%. The extract obtained is then concentrated and diluted in miglyol (25% extract/75% miglyol): we obtain 77 kg of extract at 25% miglyol. This extract then undergoes discolouring with 3% activated carbon: 77 kg of extract are thus diluted with ethanol (385 kg) to which is added 3% of activated carbon, i.e. 2.31 kg. This discolouring is carried out under agitation. Then a filtration is carried out, and the filtrate is concentrated.

The extract thus obtained is finally diluted on a miglyol-type support to standardise the ingredient at 0.5% in polygodial.

The determination of the analytical composition of the extract obtained according to example 1 is carried out by HPLC-DAD (with detection at 233 nm) and is illustrated by the chromatogram in FIG. 1 under the operating conditions described below.

HPLC-DAD Operating Conditions:
Agilent Poroshell 120 S-C18 column, 4.6×150 mm, 2.7 μm
Column temperature: 30° C.
Flow rate: 1 ml/min
30

| Injection | 3 μL |
| --- | --- |
| Concentration | 20% solubilised in methanol (HPLC grade) |

| Solvent composition |
| --- |
| A: Water/0.2% Formic acid |
| B: Acetonitrile |

| | Gradient | |
| --- | --- | --- |
| Time (min) | A % | B % |
| 0 | 95 | 5 |
| 5 | 95 | 5 |
| 60 | 5 | 95 |

Figure 1:
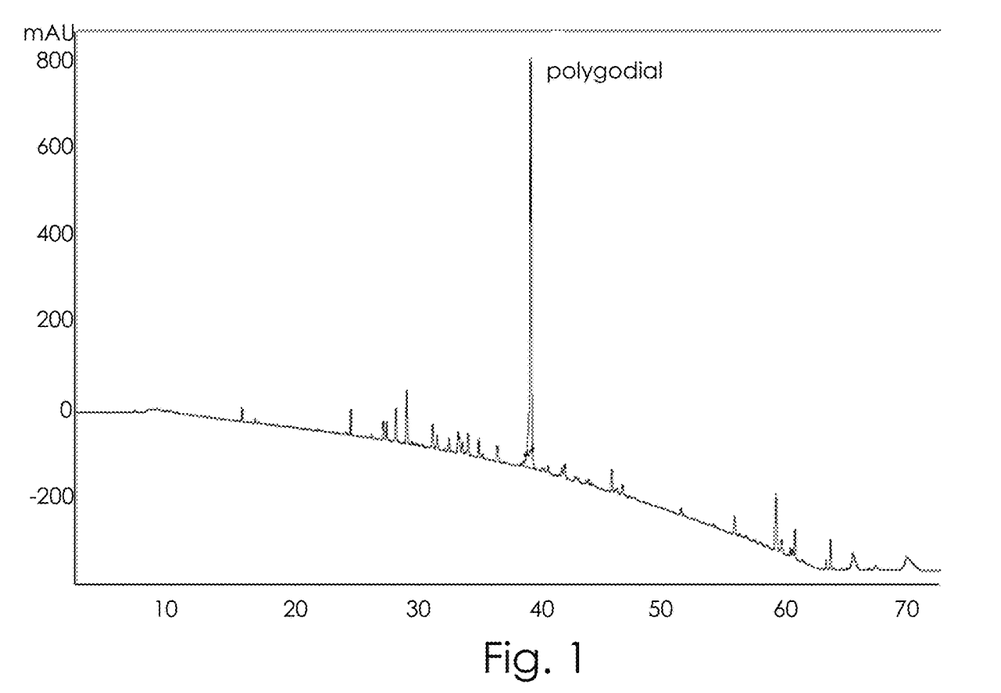
FIG. 1 shows the HPLC-DAD profile (with detection at 233 nm) of an extract of *Tasmannia lanceolata* according to the invention obtained by the process of Example 1.

As illustrated by the chromatogram in FIG. 1, the Polygodial content is 0.53% by weight of the total weight of the extract.

The extract preferably used in the composition according to the invention comprises a polygodial concentration of between 0.1% and 10%, preferably between 0.2% and 5%, more preferably between 0.5% and 3% by weight of the total weight of the extract, for example 0.5%, 1%, 1.5%, 2%, 2.5% or 3%.

Example 2

Dry Oil

| Phase | Ingredient | % | INCI name |
| --- | --- | --- | --- |
| A | *Tasmannia lanceolata* extract according to the invention | 2 | *Tasmannia lanceolata* (Tasmanian pepper) leaf extract |
| A | Dub Mct 5545 | 20 | Caprylic/capric triglyceride |
| A | Bioxan Sf T50 | 0.3 | Tocopherol & *Helianthus annuus* seed oil |
| A | Hazelnut Oil | 77.7 | Corylus avellana seed oil |

Prepare phase A: mix until the mixture is uniformly blended.

Example 3

Stretch Mark Cream for the Body

| Phase | Ingredient | % | INCI name |
| --- | --- | --- | --- |
| B | Frametime CXG | 5 | Bentonite & Xanthan gum & Sodium stearoyl glutamate & Citric acid |
| B | Mica Hs11p | 1 | mica |
| B | Amisoft | 0.4 | Sodium stearoyl glutamate |
| B | Algin | 0.15 | Algin |
| C | *Tasmannia lanceolata* extract according to the invention | 2 | *Tasmannia lanceolata* (Tasmanian pepper) leaf extract |
| C | Avocado Oil | 4 | Persea gratissima oil |
| C | Rosehip Seed Oil | 10 | Rosa Canina Seed Oil |
| D | Benzyl Alcohol | 0.35 | Benzyl alcohol |
| C1 | Kokum Butter | 4 | Garcinia indica seed butter |
| C1 | Desert Date oil | 6 | Balanites roxburghii seed oil |
| D | Perfume | 0.5 | perfume |
| D | Sodium Benzoate | 0.35 | Sodium benzoate |
| A | Glycerin | 1.5 | Glycerin |
| A | Propanediol | 5 | Propanediol |
| A | Water | 59.75 | Aqua |

Prepare phase A and mix it.
Prepare phase B and add it to the aqueous phase A. Mix until uniformly blended.
Melt phase C1 at 45° C., once it has become liquid, add to phase C and mix until uniformly blended.
Add C+C1 to A+B. Mix until uniformly blended.
Add phase D to the formula
Adjust the formulation to pH 5.0-6.0 with citric acid (50% Aq.)

Example 4

Wound Healing Cream for Acne

| Phase | Ingredient | % | INCI name |
| --- | --- | --- | --- |
| B | Frametime CX | 5 | Bentonite & Xanthan gum & Sodium stearoyl glutamate & Citric acid |

-continued

| Phase | Ingredient | % | INCI name |
|---|---|---|---|
| B | Mica | 1 | mica |
| C | HTR1 | 1.5 | Helianthus annuus seed oil & Protium heptaphyllum resin |
| C | Tasmannia lanceolata extract according to the invention | 2 | Tasmannia lanceolata (Tasmanian pepper) leaf extract |
| C | Finsolv TN | 10 | C 12-15 Alkyl Benzoate |
| C | Cetiol CC | 2 | Dicaprylyl carbonate |
| C | Desert Date oil | 6 | Balanites roxburghii seed oil |
| D | Perfume | QS | perfume |
| D | Preservatives, Fragrance | QS | Sodium benzoate |
| A | Glycerin | 1.5 | Glycerin |
| A | Propanediol | 5 | Propanediol |
| A | Water | QSP | Aqua |

Prepare phase A and mix it.
Prepare phase B, add it to the aqueous phase A. Mix until uniformly blended.
Prepare C and mix until uniformly blended
Add C to A+B. Mix until uniformly blended
Add phase D to the formula
Adjust the formulation to pH 5.0-6.0 with citric acid (50% Aq.)

Example 5

Soft Capsule

| Ingredients | Amount in mg |
|---|---|
| Extract of Tasmannia lanceolata leaves according to the invention on a vegetable oil carrier | 200-500 mg |
| Millet oil | 100-200 mg |
| Sea buckthorn oil | 100-200 mg |
| Vitamin E | 10-30 mg |

Example 6

Soft Capsule

| Ingredients | Amount in mg |
|---|---|
| Extract of Tasmannia lanceolata leaves according to the invention on a vegetable oil carrier | 100-300 mg |
| Fish oil rich in omega 3 | 200-300 mg |
| Zinc | 10-30 mg |
| Beeswax | 30-50 mg |
| Sunflower lecithin | 10-50 mg |

Example 7

Demonstration of Anti-Inflammatory Activity by Translocation of NF-kB

To evaluate the properties of a Tasmannia lanceolata extract according to the invention to modulate induced inflammation, the cells were pre-exposed to the Tasmannia lanceolata extract obtained according to example 1 at 5% in miglyol or to the SN50 peptide (a reference inhibitor for NF-kB translocation) before exposure to LPS. 24 hours after cell deposition, the fibroblasts were exposed to 5 concentrations of Tasmannia lanceolata extract or a concentration of the SN50 peptide for 24 hours. The cells were then exposed for 3 and 24 hours to LPS extracts (1 ng/mL) and Tasmannia lanceolata extract or SN50 peptide. Finally, after 3 hours of exposure, the cells were fixed and stained for NF-kB quantification.

Figure 2:
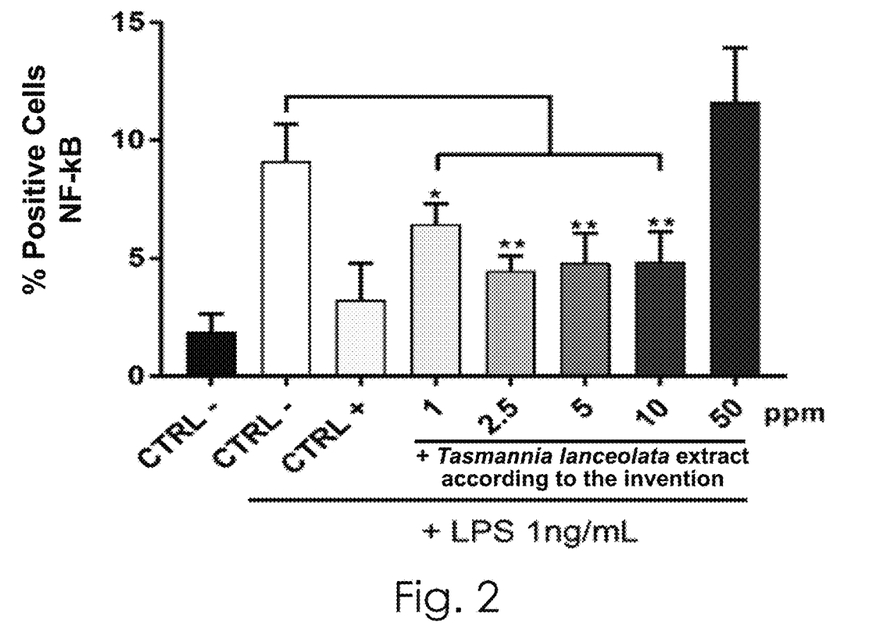
FIG. 2 represents the anti-inflammatory activity of an extract of *Tasmannia lanceolata* according to the invention on fibroblasts by the translocation of NF-kB.

The results obtained are compiled in Table 1 below and specifically illustrated in FIG. 2. It appears that the Tasmannia lanceolata extract according to the invention induces a significant decrease in the translocation of NF-kB compared to control with LPS (CTRL-), especially for these concentrations below 50 ppm.

The Tasmannia lanceolata extract according to the invention thus reduces inflammation of the skin.

TABLE 1

| ppm | CTRL– without LPS | CTRL– with LPS | CTRL+ = SN50 peptide 20 µM |
|---|---|---|---|
| % of NF-kB positive cells | 0.99 | 7.53 | 3.14 |
| | 2.82 | 8.29 | 4.88 |
| | 1.38 | 7.74 | 1.75 |
| | 2.24 | 9.53 | |
| | 2.61 | 10.12 | |
| | 1.25 | 11.55 | |
| Mean | 1.8822415 | 9.13 | 3.26 |

| ppm | Tasmannia lanceolata 1 ppm | Tasmannia lanceolata 2.5 ppm | Tasmannia lanceolata 5 ppm | Tasmannia lanceolata 10 ppm | Tasmannia lanceolata 50 ppm |
|---|---|---|---|---|---|
| % of NF-kB positive cells | 5.43 | 4.13 | 6.18 | 6.08 | 13.39 |
| | 7.0 | 5.20 | 4.56 | 4.94 | 9.03 |
| | 6.89 | 4.09 | 3.72 | 3.54 | 12.46 |
| Mean | 6.44 | 4.47 | 4.82 | 4.85 | 11.63 |

LPS at 1 ng/mL induces moderate inflammation, characterised by a significant translocation of NF-kB in 10% of the cell population compared to control alone.

The SN50 peptide (CTRL+) significantly inhibits the translocation of NF-kB induced by 1 ng/mL of LPS after 3 hours of exposure.

The Tasmannia lanceolata extract at 1, 2.5, 5 and 10 ppm does not exhibit cytotoxicity and induces a significant decrease of about 50% at 2.5, 5 and 10 ppm in the translocation of NF-kB in human fibroblasts.

Example 8

Evidence of Healing Activity by Fibroblast Migration

The cells were pre-treated with the Tasmannia lanceolata extract obtained according to example 1 at 5% in miglyol and Nucblue (live cell assay nuclei dye) in a culture medium with no growth factor. After 24 hours of pre-treatment, the cells were mechanically scratched and the medium renewed. Pictures were taken at ×4 magnification for 24 hours.

The calculations were made as follows:

$$\Delta = \text{healed surface} = \text{Surface } T0H - \text{Surface } T24H$$

where the Surface at T0 is the initial surface after scratching and the Surface at T24H is the same surface measured after 24 hours; and $$\% \text{ of healed area compared to } CTRL = \frac{\Delta \text{ treatment}}{\text{mean } (\Delta \ CTRL \text{ with no growth factors})} \times 100$$

where the treatment corresponds to the well receiving either the *Tasmannia lanceolata* extract at a given concentration or a medium containing growth factors as a positive control.

The results obtained are compiled in Table 2 below. A statistical comparison was performed between the growth factor-free control and the *Tasmannia lanceolata* extract using a T-test.

TABLE 2

| ppm | Growth factors | | | |
|---|---|---|---|---|
|  | − | + | − | − |
|  | CTL scratch | CTL + After 24 hours | *Tasmannia lanceolata* extract 1 ppm After 24 hours | *Tasmannia lanceolata* extract 2.5 ppm After 24 hours |
| % of healed area compared to control | −13.32 | 121.98 | 99.93 | 144.25 |
|  | 2.72 | 86.32 | 126.19 | 198.16 |
|  | 10.60 | 82.10 | 103.49 | 154.51 |
|  |  | 104.24 |  |  |
|  |  | 111.24 |  |  |
|  |  | 94.12 |  |  |
| Mean | 0 | 100 | 109.87 | 165.64 |

Figure 3:
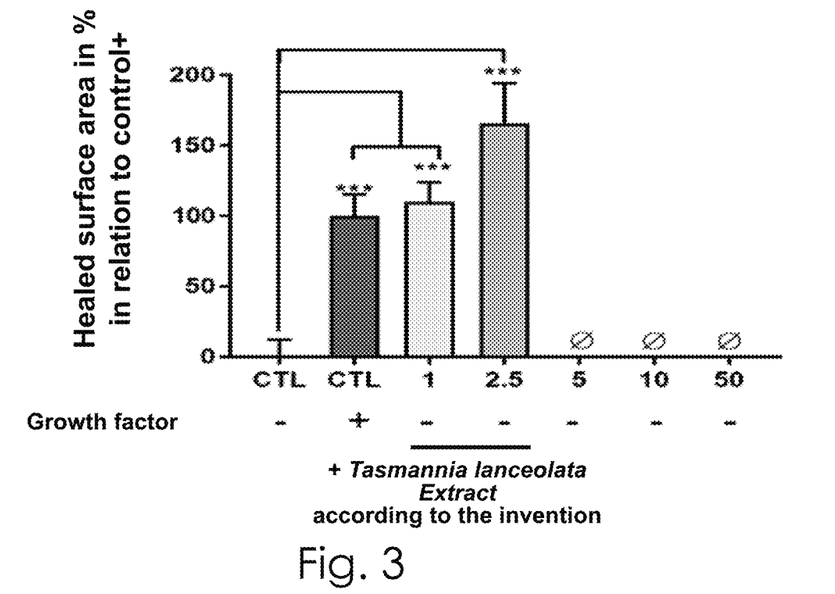
FIG. 3 represents the wound healing activity of an extract of *Tasmannia lanceolata* according to the invention by the migration of fibroblasts.
Figure 4:
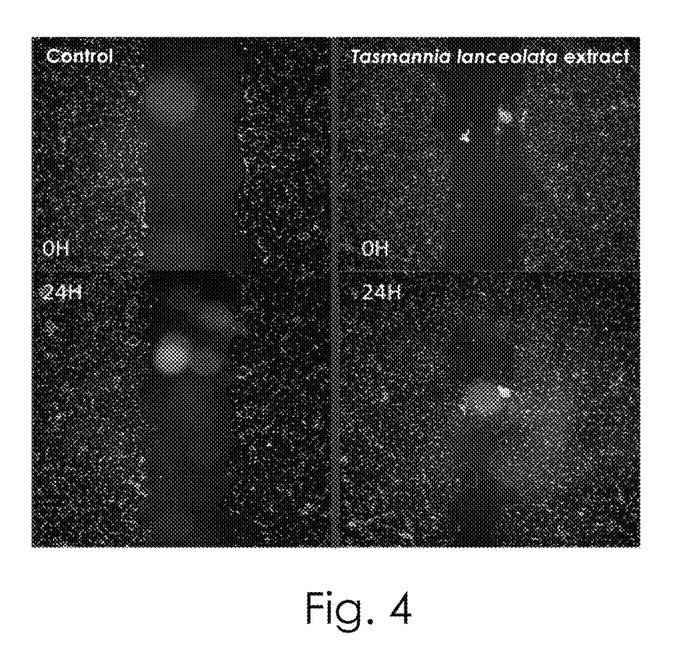
FIG. 4 shows the wound healing activity of an extract of *Tasmannia lanceolata* according to the invention (photo ×4 of the healed surface after 24 hours with and without the extract)

As shown in FIGS. 3 and 4, the Tasmanian pepper extract according to the invention induces a significant increase (+65% after 24 hours) of fibroblast migration compared to the control (with no growth factor) for concentrations of only 1 to 2.5 ppm.

Example 9

Ex-Vivo Test for the *Tasmannia lanceolata* Extract's Activity on Skin Fragments with Stretch Marks by Quantitative Analysis of TGF-β, Pro-Collagen I and Elastin Skin fragments with stretch marks from 5 different donors were placed in inserts which were then placed in culture wells. Culture medium (antibiotics, FBS) was added to the bottom of the wells, with a slow diffusion passage between the two compartments via a porous membrane (12 μm). The skin fragments were kept alive for 12 days at 37° C. and in air/CO$_2$ atmosphere.

The skin fragments were opically treated daily with the *Tasmannia lanceolata* extract according to the invention obtained according to example 1 at 5% in miglyol (15 μl/cm2).

A comparison was made between the following 2 conditions:
 skin with stretch mark (control)
 skin with stretch marks+*Tasmannia lanceolata* extract according to the invention at 2%.

| Formula no. | Solubility | Stock solution | Topically tested concentration (diluted in phosphate buttered saline) |
|---|---|---|---|
| *Tasmannia lanceolata* extract according to the invention Control | ethanol | 20% | 2% |

TGF-β Dosage:

TGF-β, synthesised in particular by keratinocytes, is a stimulation factor for the dermal fibroblast which will synthesise collagen I and III. The TGF-β dosage was analysed using an immunoassay technique with a spectrophotometric reading of the concentration (pg/ml) (BioTechne assay kits). As the skin fragments had the same surface area (verification of the weight of each fragment), the assay was carried out using the culture supernatants.

The results obtained (TGF-β concentration in pg/ml) are listed in Table 3 below:

TABLE 3

| Skin no. | Control (pg/ml) | Tasmanian pepper extract according to the invention (pg/ml) |
|---|---|---|
| 1 | 22.4 | 71.5 |
| 2 | 24.52 | 27.12 |
| 3 | 28.4 | 75.12 |
| 4 | 40.6 | 61.37 |
| 5 | 30.5 | 63.44 |
| Mean | 29.28 ± 6.33 | 59.71 ± 17.06 |
|  |  | * p = 0.0121 |

* statistical comparison with the control group

A composition comprising a *Tasmannia lanceolata* extract according to the invention induces a significant increase, on average up to more than twice, in the concentration of TGF-B in the treated skin compared to the control.

Dosage of Pro-Collagen I:

The collected skin fragments were solubilised in Tris-HCl buffer, 100 mM, NaCl 100 mM, 0.1% Triton X100, pH 7.4. After grinding with a Potter-type device, the amount of type I pro-collagen (μg/ml) was evaluated by an ELISA method (Human Pro-Collagen I alpha 1, BioTechne).

The results obtained (pro-collagen I concentration in pg/ml) are listed in Table 4 below:

TABLE 4

| Skin no. | Control (pg/ml) | Tasmanian pepper extract according to the invention (pg/ml) |
|---|---|---|
| 1 | 15.89 | 18.48 |
| 2 | 17.56 | 21.49 |
| 3 | 8.6 | 20 |
| 4 | 8.7 | 11.4 |
| 5 | 15.73 | 15.37 |
| Mean | 13.29 ± 3.84 | 17.35 ± 3.59 |
|  |  | * p = 0.05 |

* statistical comparison with the control group

A composition comprising a *Tasmannia lanceolata* extract according to the invention induces a significant increase, on average of at least 30%, in the concentration of pro-collagen 1 in the treated skin compared to the control.

Biochemical Dosage of Elastin:

Insoluble elastin is extracted from biopsies by oxalic acid at 0.25M at 100° C. as soluble fragments of alpha elastin polypeptides.

After centrifugation to remove undigested tissue, the amount of soluble elastin was measured by a spectrocolorimetric analysis method at 513 nm, after fixation of the dye 5,10,15,20-tetraphenyl-21,23-porphirin, tetrasulphonate (Fastin Elastin Assay kit, Interchim).

The results obtained (elastin concentration in µg/mg) are listed in Table 5 below:

TABLE 5

| Skin no. | Control (µg/mg) | Tasmanian pepper extract according to the invention (µg/mg) |
|---|---|---|
| 1 | 14.19 | 16.79 |
| 2 | 16.94 | 20.37 |
| 3 | 12.76 | 13 |
| 4 | 12.95 | 13.5 |
| 5 | 16 | 17.42 |
| Mean | 14.568 ± 1.656 | 16.216 ± 2.711 |
|  |  | * p = 0.0264 |

* statistical comparison with the control group

A composition comprising a *Tasmannia lanceolata* extract according to the invention induces a significant increase, on average more than 10%, in the concentration of elastin in the treated skin compared to the control.

According to the results thus obtained, a composition according to the invention comprising a *Tasmannia lanceolata* extract promotes the wound healing of the skin and, as a result, the reduction of scars and stretch marks.

Example 10

Placebo-Controlled Clinical Study to Prove the Effectiveness of a Composition Comprising a *Tasmannia lanceolata* Extract According to the Invention on Stretch Marks The study was conducted on 30 women, with an average age of 47.7 years old.

15 women received the composition comprising a *Tasmannia lanceolata* extract according to the following invention:

TABLE 6

| TASMANOL ™ oil according to the invention | | |
|---|---|---|
| Ingredient | % (w/w) | INCI name |
| TASMANOL ™® | 2 | *Tasmannia lanceolata* (Tasmanian pepper) leaf extract obtained by the process in example 1 |
| DUB MCT 5545 ® | 20 | Caprylic/capric triglyceride |
| BIOXAN SF T50 ® | 0.3 | Tocopherol & *Helianthus annuus* seed oil |
| Hazelnut oil | 77.7 | Corylus avellana seed oil |

Another 15 women received the following placebo composition; one woman was withdrawn from the study for reasons outside of the study.

TABLE 7

| Placebo | | |
|---|---|---|
| Ingredient | % (w/w) | INCI name |
| DUB MCT 55450 ® | 20 | Caprylic/capric triglyceride |
| BIOXAN SF T50 ® | 0.3 | Tocopherol & *Helianthus annuus* seed oil |
| Hazelnut oil | 79.7 | Corylus avellana seed oil |

Each composition was respectively applied twice a day to the areas presenting stretch marks (thighs, hips, stomach) for a period of two months.

The depth and colouring of stretch marks were assessed.

Measurements of the density and thickness of the dermis of stretch marks were also carried out.

Finally, the subjects carried out a self-assessment of these same criteria.

The results obtained are as follows.

Figure 5:
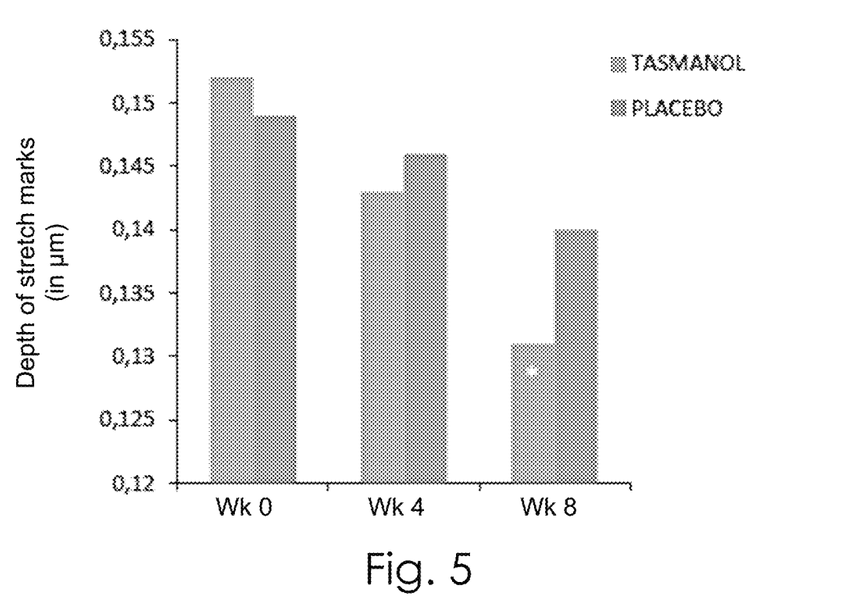
FIG. 5 represents the effectiveness of a composition comprising an extract of *Tasmannia lanceolata* obtained according to the invention in reducing the depth of stretch marks measured by the LIFEVIZ® MICRO™ 3D digital dermatology camera.
Figure 6:
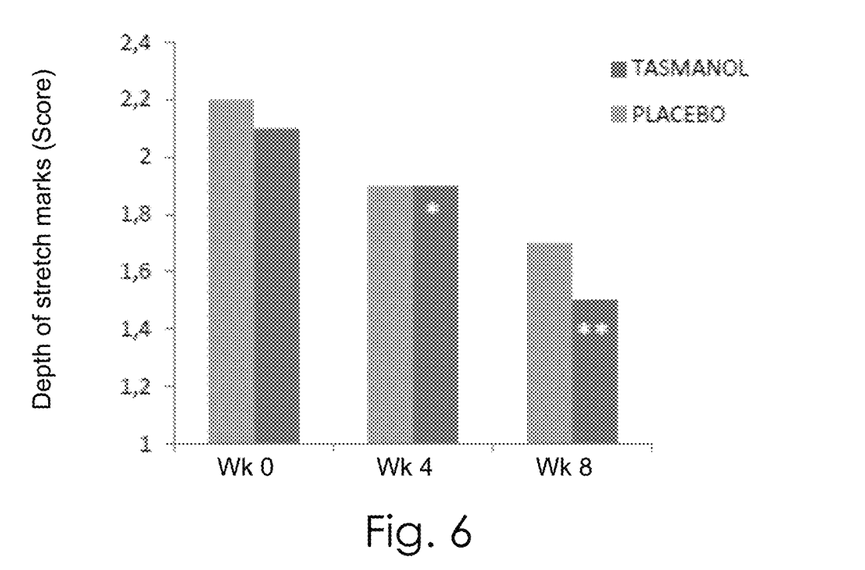
FIG. 6 represents the effectiveness of a composition comprising an extract of *Tasmannia lanceolata* obtained according to the invention in reducing the depth of stretch marks measured by clinical score (dermatologist)

As shown in FIGS. 5 and 6, after 8 weeks of daily application, the composition according to the tested invention induced a significant reduction ($p<0.05$) in the depth of stretch marks measured by the LIFEVIZ® MICRO™ 3D digital dermatology camera as well as in the clinical score ($p<0.01$) between 0 and 3 with:
0=shallow stretch marks—smooth skin;
1=slightly deep stretch marks—almost smooth skin;
2=moderately deep stretch marks—rough skin; and
3=deep stretch marks—very rough skin).

A reduction in the depth of stretch marks was observed in 80% of subjects with the tested composition according to the invention.

Figure 7:
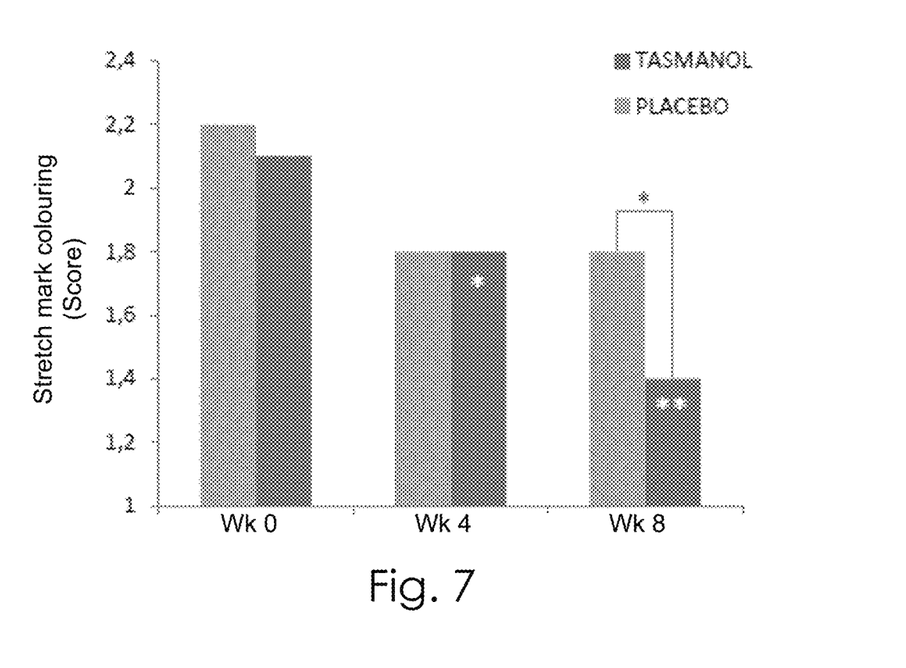
FIG. 7 represents the effectiveness of a composition comprising an extract of *Tasmannia lanceolata* obtained according to the invention in reducing the colouring of stretch marks measured by clinical score (dermatologist)

As shown in FIG. 7, after 8 weeks of daily application, the composition according to the tested invention induced a significant reduction ($p<0.01$) in the colouring of stretch marks measured by clinical score between 0 and 3 with:
0.=barely coloured stretch marks;
1=lightly coloured stretch marks;
2=moderately coloured stretch marks; and
3=coloured stretch marks A reduction in the colouring of stretch marks was observed in 66.7% of subjects with the tested composition according to the invention.

Figure 8:
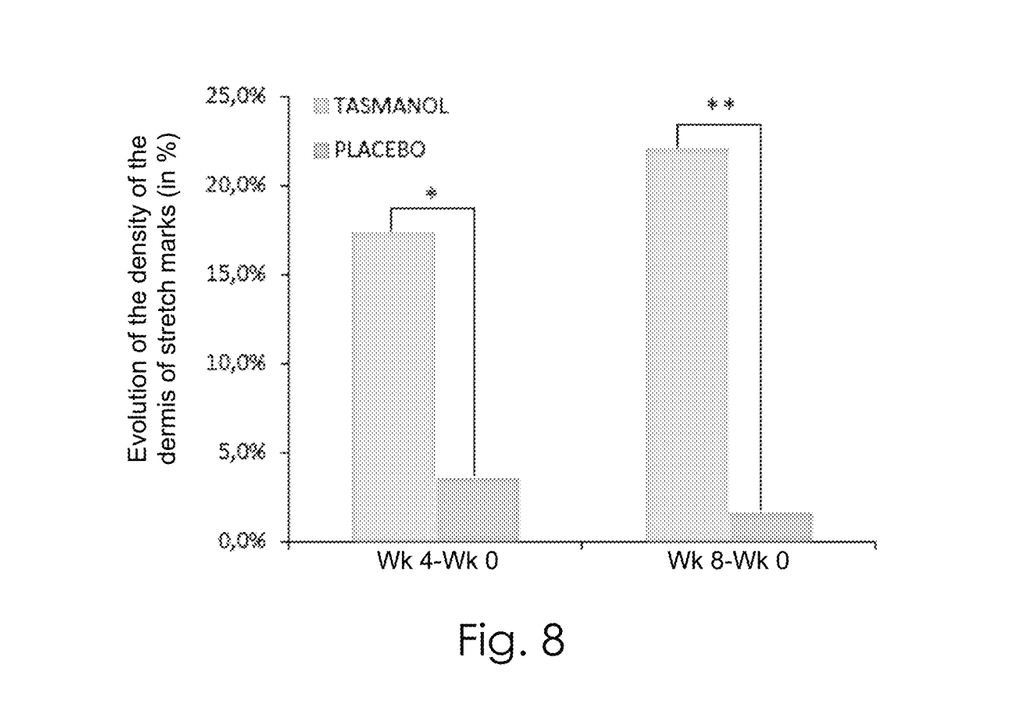
FIG. 8 represents the effectiveness of a composition comprising an extract of *Tasmannia lanceolata* obtained according to the invention in increasing the density of the dermis of stretch marks measured by ultrasound.

As shown in FIG. 8, the composition according to the invention tested induces a significant increase in the density of the dermis of stretch marks after 4 weeks of treatment ($p<0.05$) and after 8 weeks of treatment ($p<0.01$) measured by ultrasound.

An increase in the density of the dermis at the level of the stretch marks was observed in 87% of the subjects with the tested composition according to the invention.

Figure 9:
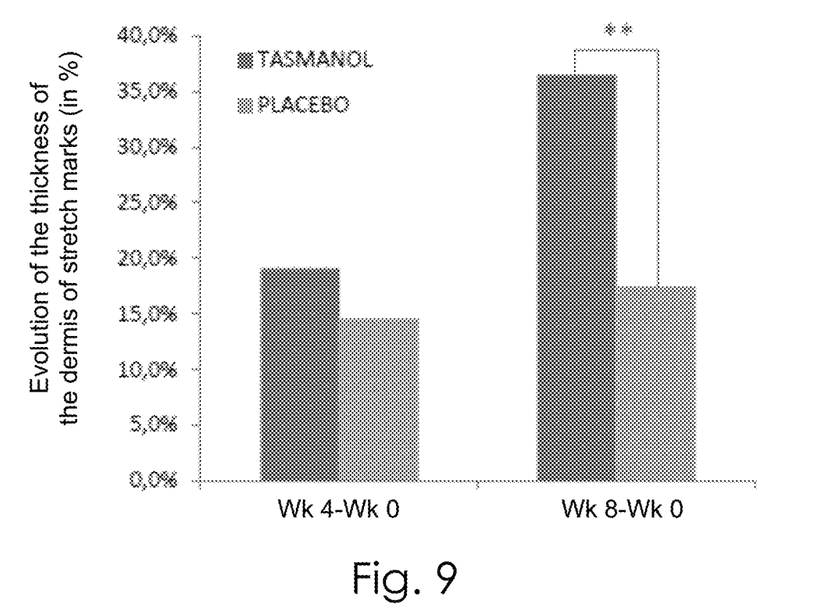
FIG. 9 represents the effectiveness of a composition comprising an extract of *Tasmannia lanceolata* obtained according to the invention in increasing the thickness of the dermis of stretch marks measured by ultrasound.

As shown in FIG. 9, the tested composition according to the invention induces a significant increase in the thickness of the dermis of stretch marks after 8 weeks of treatment ($p<0.01$) measured by ultrasound (µm).

An increase in the thickness of the dermis at the level of stretch marks was observed in 87% of the subjects with the tested composition according to the invention.

Figure 10:
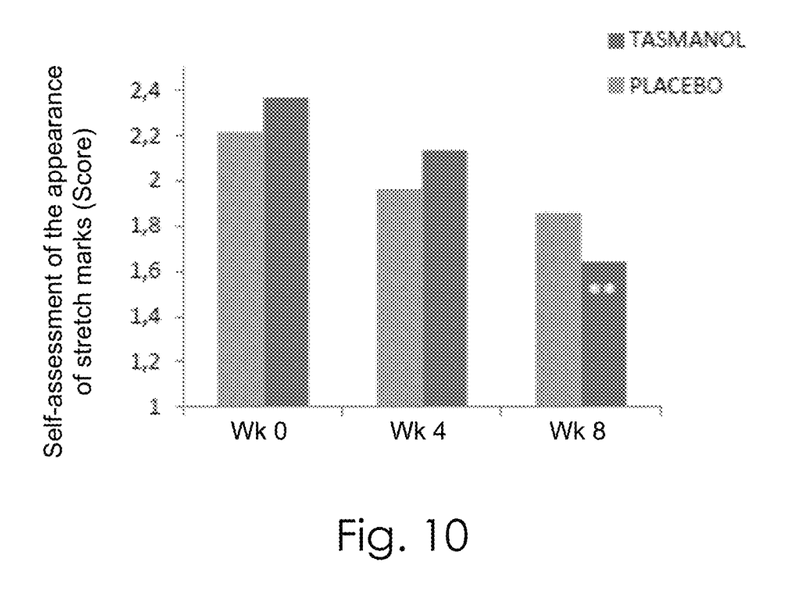
FIG. 10 represents the improvement in the appearance of stretch marks by self-assessment.

As shown in FIG. 10, after 8 weeks of daily application, subjects noted a strong improvement in the appearance of stretch marks:
stretch marks are less visible for 80% of subjects;
stretch marks are less deep for 80% of subjects;
skin is softer for 93% of the subjects;
skin is smoother for 80% of the subjects.

According to the results thus obtained, a composition comprising *Tasmannia lanceolata* extract obtained according to the invention reduces the appearance and colouring of stretch marks, reduces the depth of stretch marks, increases the density of the dermis and improves the softness of the skin.

The invention claimed is:

1. A process for obtaining an extract, comprising:
   extracting leaves or berries of a plant selected from *Tasmannia lanceolata, Drimys winteri, Spilanthes acmella* and *Polygonum hydropiper* and combinations thereof with supercritical $CO_2$ at a pressure of between 120 and 350 bar and at a temperature of between 35 and 60° C.; and
   recovering said extract, wherein the extract contains polygodial.

2. The process according to claim 1,
   wherein extracting leaves or berries comprised extracting leaves of said plant with supercritical $CO_2$ at a pressure of between 150 and 285 bar, and at a temperature of between 40 and 50° C.

3. The process according to claim 1, wherein the leaves of said plant are ground and dried before extraction.

4. The process according to claim 1, wherein said plant is *Tasmannia lanceolata.*

\* \* \* \* \*